(12) United States Patent
Baid

(10) Patent No.: US 9,877,675 B2
(45) Date of Patent: Jan. 30, 2018

(54) BLOOD COLLECTION DEVICE

(76) Inventor: Rishi Baid, New Delhi (IN)

( * ) Notice: Subject to any disclaimer, the term of this patent is extended or adjusted under 35 U.S.C. 154(b) by 869 days.

(21) Appl. No.: 13/394,638

(22) PCT Filed: Sep. 7, 2010

(86) PCT No.: PCT/IB2010/054013
§ 371 (c)(1),
(2), (4) Date: Mar. 7, 2012

(87) PCT Pub. No.: WO2011/030282
PCT Pub. Date: Mar. 17, 2011

(65) Prior Publication Data
US 2012/0172754 A1   Jul. 5, 2012

(30) Foreign Application Priority Data
Sep. 9, 2009   (IN) .......................... 1861/DEL/2009

(51) Int. Cl.
*A61B 5/00* (2006.01)
*A61B 5/15* (2006.01)
*A61B 5/153* (2006.01)

(52) U.S. Cl.
CPC ........ *A61B 5/150488* (2013.01); *A61B 5/153* (2013.01); *A61B 5/15003* (2013.01); *A61B 5/1535* (2013.01); *A61B 5/150213* (2013.01); *A61B 5/150259* (2013.01); *A61B 5/150389* (2013.01); *A61B 5/150572* (2013.01)

(58) Field of Classification Search
CPC .. A61B 5/1405; A61B 5/1438; A61B 5/15003
USPC ........................................ 600/573, 576, 579
See application file for complete search history.

(56) References Cited

U.S. PATENT DOCUMENTS

| | | | | |
|---|---|---|---|---|
| 4,929,235 A | * | 5/1990 | Merry et al. | 604/167.04 |
| 5,520,193 A | * | 5/1996 | Suzuki et al. | 600/577 |
| 5,833,662 A | * | 11/1998 | Stevens | 604/167.03 |
| 5,873,841 A | * | 2/1999 | Brannon | 600/578 |
| 5,947,932 A | * | 9/1999 | Desecki et al. | 604/190 |
| 6,355,023 B1 | * | 3/2002 | Roth et al. | 604/411 |
| 6,398,743 B1 | | 6/2002 | Halseth et al. | |
| 6,905,483 B2 | * | 6/2005 | Newby et al. | 604/164.08 |
| 7,766,879 B2 | * | 8/2010 | Tan et al. | 604/168.01 |
| 2004/0210247 A1 | * | 10/2004 | Sonoda et al. | 606/181 |
| 2005/0004524 A1 | * | 1/2005 | Newby et al. | 604/164.08 |

(Continued)

FOREIGN PATENT DOCUMENTS

| | | |
|---|---|---|
| EP | 0619096 A1 | 10/1994 |
| EP | 1579805 A1 | 9/2005 |
| JP | 2000166903 | 6/2000 |

OTHER PUBLICATIONS

European Patent Office Communication dated Feb. 16, 2012 in reference to co-pending Application No. 10 773 981.5-1526; Ref. P10401PWOEP-Sh/; Applicant: Poly Medicure Limited.

(Continued)

*Primary Examiner* — Daniel Cerioni

(57) ABSTRACT

A blood collection device comprising a cannula hub defining a chamber; an inlet cannula and an outlet cannula mounted to the cannula hub; a closed sleeve mounted over a portion of the outlet cannula; and a venting mechanism between the chamber and the ambient surroundings comprising a tubular insert and a membrane permeable to air and substantially impermeable to blood.

12 Claims, 2 Drawing Sheets

(56) References Cited

U.S. PATENT DOCUMENTS

2005/0283093 A1 12/2005 Conway et al.
2008/0167577 A1 7/2008 Weilbacher et al.
2008/0194986 A1* 8/2008 Conway et al. .............. 600/579

OTHER PUBLICATIONS

The International Bureau of WIPO; PCT International Preliminary Report on Patentability dated Mar. 13, 2012 in Reference to co-pending PCT/IB2010/054013 filed Sep. 7. 2010.

* cited by examiner

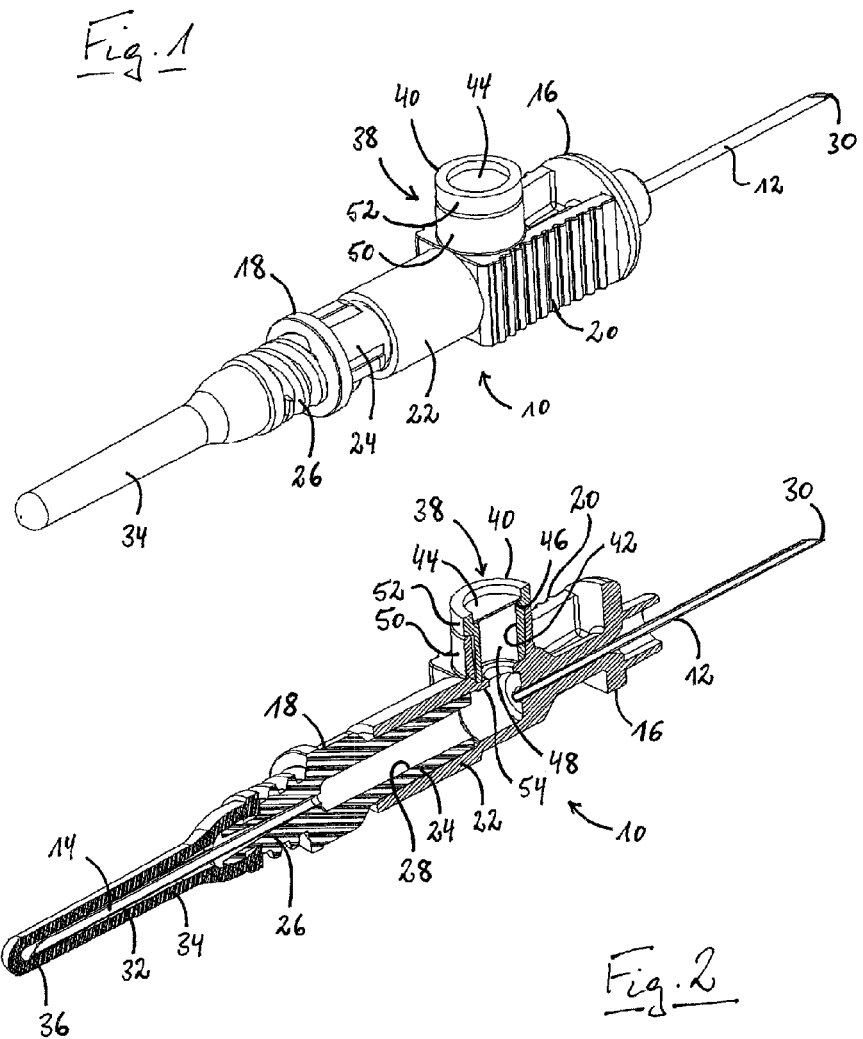

BLOOD COLLECTION DEVICE

RELATED APPLICATION INFORMATION

This application claims priority from Indian Provisional Patent Application No. 1861/DEL/2009 filed on Sep. 9, 2009. The entire content of which is incorporated herein by this reference. The applicants claim the benefit of this provisional application.

The invention relates to a blood collection device comprising a cannula hub defining a chamber, an inlet cannula and an outlet cannula both being mounted to the cannula hub and communicating with the chamber, a closed sleeve mounted over a portion of the outlet cannula disposed externally of the cannula hub, and a venting mechanism providing communication between the chamber and ambient surroundings.

Blood collection devices of the above kind have long been used to collect blood from patients, wherein the patients' vessels from which blood is to be drawn are often rather small and/or not visible. If the tip of the inlet cannula is not in communication with the interior of the blood vessel, the procedure of collecting blood is likely to be unsuccessful and the patient may be harmed additionally by the penetration of delicate underlying structures. Accordingly, confirmation of accurate placement of the cannula tip into a blood vessel is desirable for blood drawing procedures.

Known intravenous blood collection devices therefore include mechanisms for indicating when the inlet cannula tip is in communication with the interior of a blood vessel, for example, a transparent portion of the cannula hub from which the presence of blood can be observed. The observation of blood in the cannula hub is known as "flashback". However, flashback detection has been less than satisfactory for many such blood collection devices, since the flow of blood into the transparent portion of the cannula hub is impeded by air backpressure in the cannula hub and, thus, flashback confirmation is not visible or delayed. This delay can impede the determination of the precise moment at which the cannula tip enters the blood vessel, which may cause the healthcare worker inserting the needle to miss or perforate the vessel and penetrate into delicate surrounding structures. Accordingly, intravenous blood collection devices have been provided with a venting mechanism providing communication between a flashback chamber of the cannula hub and ambient surroundings.

It is an object of the invention to provide a blood collection device which allows for a more efficient use and a gentler treatment of the patient and which is easy and inexpensive to manufacture.

This object is satisfied by a blood collection device in accordance with claim 1.

The blood collection device of the invention comprises a cannula hub defining a chamber; an inlet cannula defining an axis and having a distal end and a lumen extending therethrough, the inlet cannula being mounted to the cannula hub such that the distal end of the inlet cannula is external of the cannula hub and such that the lumen through the inlet cannula communicates with the chamber; an outlet cannula having a proximal end and a lumen extending therethrough, the outlet cannula being mounted to the cannula hub such that the proximal end of the outlet cannula is external of the cannula hub and such that the lumen of the outlet cannula communicates with the chamber; a closed sleeve mounted over a portion of the outlet cannula disposed externally of the cannula hub; and a venting mechanism providing communication between the chamber and ambient surroundings, wherein the venting mechanism comprises a tubular insert defining a fluid passage therethrough and a membrane extending across the fluid passage, wherein the membrane is made from a material permeable for air and substantially impermeable for blood.

The blood collection device of the invention and, in particular, the specific design of its venting mechanism allows blood flashback to occur particularly rapidly upon entry of the inlet cannula into the blood vessel. This makes particularly quick and reliable venipuncture detection possible and, thus, helps to ensure that the inlet cannula is correctly placed in the patient on the first try. In the end, blood can be collected with the device of the invention in a manner that is particularly gentle on the patient.

According to the invention, the inlet cannula and the outlet cannula can either be two separate parts or they can be integrally formed from a single cannula that is provided with an opening in the region of the flashback chamber which allows for communication between both the lumen of the inlet cannula and the lumen of the outlet cannula with the flashback chamber.

Furthermore, the membrane can be configured such that upon contact with blood the membrane either remains permeable for air or becomes impermeable not only for blood but also for air. In the latter case the membrane could be referred to as self-sealing.

According to an embodiment of the invention, the tubular insert of the venting mechanism is received in a tubular projection extending from the cannula hub. Preferably, the tubular projection extends in a direction transverse, in particular perpendicular, to the axis of the inlet cannula.

The manufacturing of the device is particularly simple and inexpensive, if the tubular projection is integral with the cannula hub, in particular with a first part of the cannula hub carrying the inlet cannula.

According to a further embodiment, the tubular insert of the venting mechanism is fixed in the tubular projection by means of a press fit. This makes the assembly of the device particularly simple and cost effective, since the venting mechanism can be prepared separately from the cannula hub, whereupon the tubular insert has merely to be pushed into the tubular projection.

In order to prevent the tubular insert from being pushed too far into the tubular projection, the tubular insert of the venting mechanism may have a collar formed on its outer surface adjacent an end facing away from the cannula hub. In addition, the collar fulfils a sealing function as it helps to prevent blood from exiting the flashback chamber.

Preferably, an outer diameter of the collar is substantially equal to an outer diameter of the tubular projection, since this leads to a smooth transition from collar to tubular projection in the assembled state.

According to a further embodiment, the fluid passage is diminished by an inner collar in the region of the tubular projection adjacent the chamber of the cannula hub. This inner collar adds to the sealing function in that it also helps to prevent blood from exiting the flashback chamber.

According to another embodiment, the cannula hub is formed from first and second parts, the first part carrying the inlet cannula and the second part carrying the outlet cannula.

Preferably, the first part comprises a grip portion and a tubular portion extending proximal therefrom in the direction of the cannula axis. The grip portion makes the handling of the device easier, while the tubular portion extending therefrom may be designed to give a clear view on blood entering the flashback chamber.

According to a further embodiment, the second part is of generally tubular shape and partly received in the tubular portion of the first part by means of a press fit. Thus, the second part needs only to be pushed into the first part for assembly of the device, which adds to the simple and cost effective manufacturing of the device.

Preferably, the second part and at least the tubular portion of the first part are made from a transparent plastic material. This simplifies flashback detection and makes the manufacturing of the device even more cost effective, since the first and second parts can be made by injection molding and no additional windows for flash back detection have to be implemented.

A preferred embodiment of the invention is described in the following description and in the accompanying drawings, wherein:

FIG. 1 is a perspective view of a blood collection device in accordance with the invention;

FIG. 2 is a cross sectional view of the blood collection device of FIG. 1; and

Figure 3:
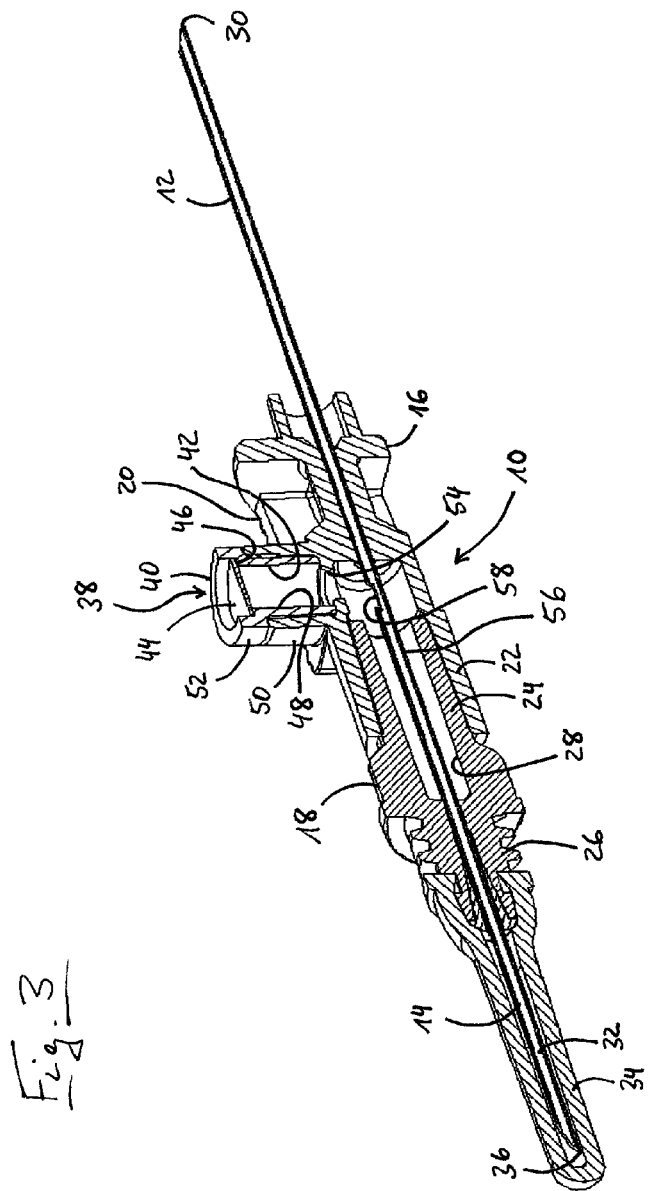
FIG. 3 is a cross sectional view of a blood collection device according to a further embodiment of the invention.

The blood collection device shown in FIGS. 1 and 2 comprises a cannula hub 10 which carries an inlet cannula 12 and an outlet cannula 14. Inlet and outlet cannulas 12, 14 are aligned and define a needle axis. According to this embodiment, the inlet cannula 12 and the outlet cannula 14 form separate parts.

The cannula hub 10 is formed from a first part 16 and a second part 18. Both the first and second parts 16, 18 are made from a transparent plastic material, e.g. by injection molding.

The first part 16 includes a distal grip portion 20 for easy handling of the blood collection device, and a tubular portion 22 extending proximal therefrom.

The second part 18 includes a tubular portion 24 and a threaded portion 26 extending proximal therefrom. The tubular portion 24 of the second part 18 has a slightly tapered outer surface and is received in the tubular portion 22 of the first part 16 by means of a press fit. The threaded portion 26 makes it possible to attach a blood collection tube, bag, container or the like (not shown) to the device.

The tubular portions 22, 24 of the first and second parts 16, 18 together define a flashback chamber 28 of the cannula hub 10.

The inlet cannula 12 has a tip 30 at its distal end which is adapted to be inserted into a patient's blood vessel for drawing blood. The inlet cannula 12 is mounted to the first part 16 of the cannula hub 10 such that its lumen communicates with the flashback chamber 28.

The outlet cannula 14 is mounted to the second part 18 of the cannula hub 10 such that a lumen of the outlet cannula 14 communicates with the flashback chamber 28. The outlet cannula 14 has a proximal portion 32 extending from the second part 18 of the cannula hub 10 which is adapted to be inserted into an blood collection tube, bag, container or the like (not shown) for collecting blood from the flashback chamber. The proximal portion 32 of the outlet cannula 14 is covered by a rubber sleeve 34. The outlet cannula 14 has a tip 36 at its proximal end for puncturing the rubber sleeve 34 when the blood collection tube, bag, container or the like is to be connected to the device.

The blood collection device further comprises a venting mechanism 38 providing communication between the flashback chamber 28 and ambient surroundings.

The venting mechanism 38 comprises a tubular insert 40 defining a fluid passage 42 therethrough, and a membrane 44 extending across the fluid passage 42. The membrane 44 sits on a shoulder 46 extending along the inner surface 48 of the tubular insert 40 and may be attached to the tubular insert 40, for example, by gluing, welding, etc.

The membrane 44 is made from a material permeable for air and substantially impermeable for blood. The membrane 44 can be configured such that upon contact with blood the membrane 44 either remains permeable for air or becomes impermeable not only for blood but also for air. Examples for suitable materials include but are not limited to plastic, thermoplastic and polyethylene.

The tubular insert 40 of the venting mechanism 38 is received in a tubular projection 50 which is formed integral with the first part 16 of the cannula hub 10. The tubular projection 50 extends perpendicularly to the needle axis from the first part 16 of the cannula hub 10, more specifically in the proximal region of the grip portion 20 thereof.

The tubular insert 40 of the venting mechanism 38 is fixed in the tubular projection 50 by means of a press fit. An outer collar 52 is formed at an outer surface of the tubular insert 40 adjacent an end of the tubular insert 40 facing away from the cannula hub 10. The outer diameter of the collar 52 is substantially equal to an outer diameter of the tubular projection 50.

In the transition region from the tubular projection 50 to the flashback chamber 28, an inner collar 54 is provided. The length of the tubular insert 40 is selected such that the outer collar 52 abuts on the end of the tubular projection 50 facing away from the flashback chamber 28, while the end of the tubular insert 40 facing towards the flashback chamber 28 abuts on the inner collar 54, when the tubular insert 40 is fully inserted into the tubular projection 50.

In use, when the inlet cannula 12 is inserted into the blood vessel of a patient blood enters the inlet cannula 12 due to the blood pressure, thereby displacing air from the lumen of the inlet cannula 12 into the flashback chamber 28. Instead of being compressed in the flashback chamber 28 and thereby building up backpressure, the displaced air can escape from the flashback chamber 28 via the membrane 44 of the venting mechanism 38, such that the blood in the inlet cannula 12 is free to flow into the flashback chamber thereby indicating successful venipuncture. At the same time, membrane 44 as well as the press fit of the tubular insert 40 in the tubular projection 50 together with the outer and inner collars 52, 54 prevent blood from escaping the flashback chamber 28 via the venting mechanism 38.

FIG. 3 illustrates another embodiment of a blood collection device in accordance with the invention, which is essentially identical to the blood collection device shown in FIGS. 1 and 2 except for the fact that the inlet cannula 12 and the outlet cannula 14 do not form separate parts. Instead, in the blood collection device of FIG. 3 the inlet cannula 12 and the outlet cannula 14 are integrally formed from a single cannula 56 provided with an opening 58 that not only distinguishes the inlet cannula 12 from the outlet cannula 14 but also allows for communication between both the lumen of the inlet cannula 12 and the lumen of the outlet cannula 14 with the flashback chamber 28. The opening 58, e.g. a slot or a puncture, can be positioned anywhere in the region of the flashback chamber 28.

LIST OF REFERENCE NUMERALS 10 cannula hub
12 inlet cannula
14 outlet cannula
16 first part 18 second part
20 grip portion
22 tubular portion
24 tubular portion
26 threaded portion
28 flashback chamber
30 tip
32 proximal portion
34 rubber sleeve
36 tip
38 venting mechanism
40 tubular insert
42 fluid passage
44 membrane
46 shoulder
48 inner surface
50 tubular projection
52 outer collar
54 inner collar
56 single cannula
58 opening

What is claimed is:

1. A blood collection device comprising:
a cannula hub defining a chamber, said cannula hub further comprising a tubular projection extending outwardly from said cannula hub;
an inlet cannula defining an axis and having a distal end, the inlet cannula being mounted to the cannula hub such that the distal end of the inlet cannula is external of the cannula hub;
an inlet lumen extending through the inlet cannula such that said inlet lumen communicates with the chamber;
an outlet cannula having a proximal end, the outlet cannula being mounted to the cannula hub such that the proximal end of the outlet cannula is external of the cannula hub;
an outlet lumen extending through the outlet cannula such that said outlet lumen communicates with the chamber;
a closed sleeve mounted over a portion of the outlet cannula disposed externally of the cannula hub; and
a venting mechanism providing communication between the chamber and ambient surroundings, said venting mechanism further comprising a tubular insert and a membrane;
wherein:
at least a portion of the tubular insert of the venting mechanism is contained within the tubular projection of the cannula hub;
the tubular insert defines a fluid passage;
the membrane extends across said fluid passage; and
the membrane is made from a material permeable for air and substantially impermeable for blood.

2. The blood collection device of claim 1, wherein the tubular projection extends in a direction transverse to the axis of the inlet cannula.

3. The blood collection device of claim 1, wherein the tubular projection is integral with a first part of the cannula hub carrying the inlet cannula.

4. The blood collection device of claim 1, further comprising a press fit that fixes the tubular insert of the venting mechanism to the tubular projection.

5. The blood collection device of claim 1, wherein the tubular insert of the venting mechanism comprises an outer collar formed at an outer surface of the tubular insert adjacent an end of the tubular insert that faces away from the cannula hub.

6. The blood collection device of claim 5, wherein an outer diameter of the outer collar is greater than an inner diameter of the tubular projection and substantially equal to an outer diameter of the tubular projection, wherein the inner diameter of said tubular projection is configured to receive at least a portion of said tubular insert.

7. The blood collection device of claim 1, further comprising an inner collar that diminishes the fluid passage in a region of the tubular projection adjacent the chamber of the cannula hub.

8. The blood collection device of claim 1, wherein the cannula hub is formed from first and second parts, the first part configured to mount the inlet cannula, and the second part configured to mount the outlet cannula.

9. The blood collection device of claim 8, wherein the first part comprises a grip portion and a tubular portion extending proximal from the grip portion in the direction of the cannula axis.

10. The blood collection device of claim 8, wherein:
the second part has a generally tubular shape; and
a portion of the second part is received in the tubular portion of the first part by a press fit.

11. The blood collection device of claim 8, wherein the second part and at least the tubular portion of the first part are made from a transparent plastic material.

12. A blood collection device comprising:
a cannula hub defining a chamber, said cannula hub further comprising a tubular projection;
an inlet cannula defining an axis and having a distal end, the inlet cannula being mounted to the cannula hub such that the distal end of the inlet cannula is external of the cannula hub;
an inlet lumen extending through the inlet cannula such that said inlet lumen communicates with the chamber;
an outlet cannula having a proximal end, the outlet cannula being mounted to the cannula hub such that the proximal end of the outlet cannula is external of the cannula hub;
an outlet lumen extending through the outlet cannula such that said outlet lumen communicates with the chamber;
a closed sleeve mounted over a portion of the outlet cannula disposed externally of the cannula hub; and
a venting mechanism providing communication between the chamber and ambient surroundings, said venting mechanism further comprising a tubular insert and a membrane;
wherein:
at least a portion of the tubular insert of the venting mechanism is contained within the tubular projection of the cannula hub;
the tubular insert defines a fluid passage;
the tubular insert comprises an outer collar formed at an outer surface of the tubular insert adjacent an end of the tubular insert that faces away from the cannula hub;
an outer diameter of the outer collar is substantially equal to an outer diameter of the tubular projection;
the membrane extends across said fluid passage; and
the membrane is made from a material permeable for air and substantially impermeable for blood.

* * * * *